(12) United States Patent
Fein et al.

(10) Patent No.: US 9,833,434 B2
(45) Date of Patent: *Dec. 5, 2017

(54) METHODS OF TREATING SKIN CONDITIONS USING CYCLOLIGNAN COMPOUNDS

(71) Applicant: m. Alphabet 2, L.L.C., Delray Beach, FL (US)

(72) Inventors: Howard Fein, Redondo Beach, CA (US); Joshua M. Berlin, Boca Raton, FL (US)

(73) Assignee: m. Alphabet 2, L.L.C., Delray Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,238

(22) Filed: Apr. 20, 2015

(65) Prior Publication Data

US 2015/0231111 A1 Aug. 20, 2015

Related U.S. Application Data

(63) Continuation of application No. PCT/US2014/037523, filed on May 9, 2014.

(60) Provisional application No. 61/822,072, filed on May 10, 2013.

(51) Int. Cl.
*A61K 31/365* (2006.01)
*A61K 45/06* (2006.01)

(52) U.S. Cl.
CPC .......... *A61K 31/365* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,739,114 | A | 4/1998 | Gordaliza et al. |
| 7,348,358 | B2 | 3/2008 | Axelar |
| 7,629,381 | B2 | 12/2009 | Larsson et al. |
| 7,662,851 | B2 | 2/2010 | Larsson et al. |
| 7,709,526 | B2 | 5/2010 | Larsson et al. |
| 8,158,809 | B2 | 4/2012 | Yang |
| 8,389,747 | B2 | 3/2013 | Larsson et al. |
| 2004/0167208 | A1* | 8/2004 | Larsson ............ A61K 31/36 514/464 |
| 2005/0009759 | A1 | 1/2005 | Monneret et al. |
| 2006/0154982 | A1* | 7/2006 | Larsson ............ A61K 31/34 514/464 |
| 2009/0093488 | A1 | 4/2009 | Buck |
| 2009/0271879 | A1 | 10/2009 | Berkowitz et al. |
| 2010/0216728 | A1 | 8/2010 | Larsson et al. |
| 2013/0245285 | A1 | 9/2013 | Axelsson et al. |
| 2013/0317099 | A1* | 11/2013 | Bisrat ............ A61K 31/365 514/463 |
| 2013/0331445 | A1* | 12/2013 | Bisrat ............ C07D 493/04 514/463 |
| 2014/0255522 | A1* | 9/2014 | Lozinsky .......... A61K 31/5375 424/725 |
| 2015/0231111 | A1 | 8/2015 | Fein |

FOREIGN PATENT DOCUMENTS

| | | |
|---|---|---|
| WO | WO-2009/100349 A1 | 8/2009 |
| WO | WO-2011/107939 A1 | 9/2011 |
| WO | WO-2013/001080 A1 | 1/2013 |

OTHER PUBLICATIONS

Decraene et al. (Sep. 6, 2002 The Journal of Biological Chemistry, 277, 32587-32595).*
Einspahr et al. (Cancer Epidemiology, Biomarkers & Prevention, vol. 6, 583-587. Aug. 1997).*
Shin et al. (Cancer Lett. Jan. 28, 2010;287(2):231-9. Epub Jul. 17, 2009).*
Berkowitz et al., "Enzyme-assisted asymmetric total synthesis of (-)-podophyllotoxin and (-)-picropodophyllin," *J. Org. Chem.*, Feb. 11, 2000, 65(3):847-860.
Clayburgh et al., "The Effects of Epidermal Growth Factor Receptor and Insulin-like Growth Factor 1 Receptor Inhibition on Proliferation and Intracellular Signaling in cSCCHN: Potential for Dual Inhibition as a Therapeutic Modality," *Head Neck*, Jan. 2013, 35(1):36-93.
Economou et al., "Oral Picropodophyllin (PPP) Is Well Tolerated In Vivo and Inhibits IGF-1R Expression and Growth of Uveal Melanoma," *Invest. Ophthalmol. Vis. Sci.*, Jun. 2008, 49(6):2337-2342.
Guo et al., "Biotransformation of podophyllotoxin to picropodophyllin by microbes," *J. Asian Not. Prod. Res.*, 1998, 1(2):99-102.
Nagar et al., "Podophyllotoxin and Their Glycosidic Derivatives," *Pharmacophore*, 2011, 2(2):124-134.
Stadler et al., "Concise stereoselective synthesis of (-)-podophyllotoxin by an intermolecular iron(III)-catalyzed Friedel-Crafts alkylation," *Angew. Chem. Int. Ed. Engl.*, 2008, 47(39):7557-7559.
Vitale et al., "New picropodophyllin analogs via palladium-catalyzed allylic alkylation-Hiyama cross-coupling sequences," *J. Org. Chem.*, Aug. 1, 2008, 73(15)5795-5805.
International Search Report dated Sep. 25, 2014, from International Patent Application No. PCT/US2014/0372523, 4 pages.
Baxter, et al., "Antiproliferative and pro-apoptotic activities of insulin-like growth factor-binding protein-3," Growth Hormone & IGF Research (2000) Supplement A, S10-S11.
Criscione, et al., "Actinic Keratoses," Cancer (Jun. 1, 2009) 2523-2530.
Frost, et al., "High Incidence and Regression Rates of Solar Keratoses in a Queensland Community," J. Invest. Dermatol., 115:273-277.
Gunduz, et al., "Comparison of Growth Hormone Receptor, IGF-1R and IGFBP-3 Between Tumoral and Non-Tumoral Areas in Non-Melanoma Skin Cancers," Turkish Journal of Pathology (2013) 29:185-192.

(Continued)

*Primary Examiner* — Kortney L. Klinkel
*Assistant Examiner* — William Y Lee
(74) *Attorney, Agent, or Firm* — Duane Morris LLP; Vicki Norton; Ryan Smith

(57) ABSTRACT

The present invention includes compositions and methods for the treatment of skin conditions by administration of a cyclolignan such as picropodophyllin and/or a derivative, metabolite, analog, prodrug, pharmaceutically acceptable salt, or hydrate thereof.

6 Claims, No Drawings

(56) References Cited

OTHER PUBLICATIONS

Kubo, et al., "p53 Gene Mutations in Human Skin Cancers and Precancerous Lesions: Comparison with Immunohistochemical Analysis," J. Invest. Dermatol. (Apr. 1994) 102(4):440-444.

Marks, et al., "Malignant Transformation of Solar Keratoses to Squamous Cell Carcinoma," The Lancet (Apr. 9, 1988) 1(8589;759-7.

Nakazawa, et al., "UV and skin cancer: Specific p53 gene mutation in normal skin as a biologically relevant exposure measurement," Proc. Natl. Acad. Sci. (Jan. 1994) 91:360-364.

Oh, et al., "Expression of Insulin-like Growth Factor-1 Receptor in Conventional Cutaneous Squamous Cell Carcinoma With Different Histological Grades of Differentiation," Am. J. Dermatopathol. (Oct. 2014) 36(10)807-811.

Ananthaswamy, H.N., "Sunlight and skin cancer", Journal of Biomedicine and Biotechnology (2001) 1:2, p. 49.

Fong, A. Picropodophyllin downregulates p53 and increases the Warburg effect in pediatric glioblastoma cells. [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr 5640, in 2 pages.

Braun-Falco, M. "Hauttumoren im Gesichtsbereich", HNO; Deutsche Gesellschaft Fur Hals-Nasen-Ohren-Heilkunde, Kopfund Hals-Chirurgie, Springer, Berlin, DE, vol. 57, No. 4, Mar. 27, 2009, pp. 302-314.

European Search Report in European Patent Application No. 1479547.7, dated Jan. 2, 2017, in 8 pages.

Stockfleth, E., "The paradigm shift in treating actinic keratosis: a comprehensive strategy," Journal of Drugs in Dermatology: JDD Dec. 2012, vol. 11, No. 12, Dec. 2012, pp. 1462-1467.

Chen, et al. IGF-1R as an anti-cancer target—trials and tribulations. Chin J Cancer (2013). 32(5) 242-252.

Chetty, et al., Primary Care Review of Actinic Keratosis and Its Therapeutic Options: A Global Perspective. Dermatol Ther (Heidelb), (2015) 5:19-35.

Ekman et al., A novel oral insulin-like growth factor-1 receptor pathway modulator and its implications for patients with non-small cell lung carcinoma: A phase I clinical trial. Acta Oncologica (2016). 55(2): 140-148.

Goldenberg et al., Actinic Keratosis. Journal of Clinical Aesthetic Dermatology (2014). 7(10):28-31.

Lewis, D.A., Reversing the aging stromal phenotype prevents carcinoma initiation, Aging, Apr. 2011, 3(4), 407-416.

Lewis, J. Invest. Dermatol. 2009, 129 (3), 787,791.

Medina et al., Biochemical Pharmacology 2003, 66, 1885-1895.

Moher et al., Podophyllum Toxicity: Case Report and Literature Review. Journal of Family Practice (1979) 9(2):237-240.

Nashan et al., Therapeutic strategies for actinic keratoses—a systematic review. EurJ Dermatol (2013). 23(1): 14-32.

Physician's Desk Reference webpage describing Condylox Gel (podofilox), at http://www.pdr.net/drug-summary/Condylox-Gel-podofilox-2984?mode=preview, downloaded Dec. 20, 2016, in 3 pages.

Ratushny et al., Journal of Clinical Investigation 2012, 122 (2), 464-472.

Robertson, K. et al., Variation in Epidermal Morphology in Human Skin at Different Body Sites as Measured by Reflectance Confocal Microscopy, Acta Derm Venereol 2010; 90:368-373.

Slater et al., Podophyllin Poisoning: Systemic Toxicity Following Cutaneous Application. Obstetrics and Gynecology (1978). 51(1):94-96.

Werner et al., Evidence- and consensus-based (S3) Guidelines for the Treatment of Actinic Keratosis—International League of Dermatological Societies in cooperation with the European Dermatology Forum—Short version. JEADV (2015). vol. 29, 2069-2079.

Williams et al. Advanced Drug Delivery Reviews 2004, 56, 603-618.

* cited by examiner

METHODS OF TREATING SKIN CONDITIONS USING CYCLOLIGNAN COMPOUNDS

RELATED APPLICATIONS

The present application is a continuation application of International PCT Application Serial No. PCT/US14/37523, filed on May 9, 2014, which claims the benefit of U.S. Provisional Patent Application Ser. No. 61/822,072, filed on May 10, 2013, each of with are incorporated herein in their entirety.

FIELD OF THE INVENTION

The present invention is directed to methods of treating various skin conditions by administering to a patient a composition that includes a cyclolignan compound such as picropodophyllin, either alone or in combination with one or more additional active ingredients.

BACKGROUND OF THE INVENTION

Hyperproliferative skin diseases are a common dermatologic problem and include both benign and malignant skin conditions. Benign hyperproliferative skin conditions include such entities as common warts (verruca vulgaris), flat warts (verruca plana), seborrheic keratosis, actinic keratosis, psoriasis, certain types of ichthyosis, genital warts (condyloma accuminatum), molluscum contagiosum, and acanthosis nigricans. Malignant hyperproliferative skin conditions include such entities as basal cell carcima, squamous cell carinoma, squamous cell carcinoma in situ (Bowen's disease), melanoma, and sarcoma.

Various treatments for hyperproliferative skin conditions including physical destructive modalities and pharmacologic treatment. Commonly used physical destructive techniques include cryotherapy, electrosurgery, laser surgery, dermabrasion, and chemical ablation. Commonly used phamacologic treatments for hyperproliferative skin conditions include topical fluorouracil, imiquimod, alpha and beta hydroxy acids, cantharidin, corticosteroids, ingenol menbutate, and tretinoin. While these topical pharmacologic treatments are at times effective, many are limited by the adverse side-effect profile including extreme irritation (ingenol mebutate and fluorouracil), modest efficacy (imiquimod), and systemic toxicity (cantharidin). Because of these limitations with existing topical treatments for hyperproliferative skin conditions, physicians for years have sought to develop alternative pharmacologic treatments with enhanced efficacy and decreased side-effects.

SUMMARY OF THE INVENTION

The present invention provides compositions that include picropodophyllin (or a derivative thereof, as described further herein) and methods of using these compositions in the treatment of various skin conditions. The methods include administering, to a patient, a composition (e.g., a pharmaceutical composition) comprising picropodophyllin and/or any one or more of a pharmacologically acceptable precursor, prodrug, or other derivative thereof. In lieu of a method of treatment, the invention can be described as the use of the present compositions in the preparation of a medicament (e.g., in the preparation of a medicament for the treatment of a condition described herein).

Picropodophyllin derivatives useful in the methods of the invention include isomers, epimers, salts, esters and analogs, that have for example, ring modifications or ring substitutions as described further below. Also included are hydrates, polymorphs, glycosides and prodrugs, as well as related compounds such as etoposide, teniposide, demethoxyepi-isopicropodophyllin, tafluposide, etopophos, NK611 and their derivatives. The derivatives useful in the methods and uses of the current invention are described, for example, by Vitale et al., (Journal of Organic Chemistry, 73:5795-5805, 2008; Nagar et al., Pharmacophore 2(2):124-134, 2011; U.S. Pat. Nos. 5,739,114; 7,629,381, 7,662,851; 7,709,526; 8,158,809; and 8,389,747; United States Patent Application Nos. US20050009759 and US20100216728; and International Patent Application Publication Nos. WO/2013132262 and WO/2013132263. The content of these references is incorporated herein by reference in its entirety.

Picropodophyllin derivatives useful in the methods of the invention may be prepared from podophyllin or podophyllotoxin using methods known to one of ordinary skill in the art (for example, see Stadler and Bach, Angew. Chem, Int. Ed. Engl., 47(39):7557, 2008); Berkowitz et al. J. Org. Chem. 65:847-860, 2000; United States Patent Application Nos. US20090271879 and US20130245285 (which are incorporated herein by reference in their entirety); and Vitale et al. Journal of Organic Chemistry, 73:5795-5805, 2008).

In one embodiment, the methods include administering a pharmaceutical or physiologically acceptable composition that includes a therapeutically effective amount of picropodophyllin and/or one or more of its pharmaceutically acceptable derivatives. Such a composition and others described herein can be administered to treat one or more of the following skin or medical conditions: verruca (warts), actinic keratosis, condyloma, molluscum contagiosum, squamous cell carcinoma, basal cell carcinoma, squamous cell carcinoma in situ, melanoma, acanthosis nigricans, porokeratosis, seborrheic keratosis, fibroepithelial polyp (skin tag), melasma, angiosarcoma, Kaposi's sarcoma, sarcoma, acne (e.g., vulgaris, comedonal acne vulgaris, or cystic acne vulgaris) and conditions related thereto (e.g., scarring), perioral dermatitis, trichoepithelliomas and related genetic syndromes that cause multiple trichoepithelliomas and dermatofibrosarcoma protuberans in a patient.

In another aspect, the invention features pharmaceutical compositions that include (a) picropodophyllin, another compound described herein, and/or a pharmaceutically acceptable derivative thereof (in, for example, therapeutically effective amounts), and (b) a second anti-neoplastic agent (e.g., fluorouracil, imiquimod, or ingenol mebutate) (in, for example, a therapeutically effective amount). The compositions can be formulated as described herein. For example, they can be formulated for topical application and may include propylene glycol

DETAILED DESCRIPTION

The methods of the invention can be carried out by administering to a patient a compound of Formula I or a pharmaceutically acceptable derivative thereof:

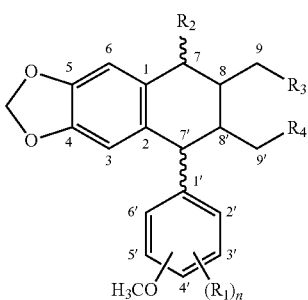

Picropodophyllin is a member of the class cyclolignan family of compounds. It contains a fused cyclic ring system and four adjacent chiral centers. In Formula I, each $R_1$ can be the same or different and can be OH or $OCH_3$, where n is 0, 1 or 2. $R_2$, $R_3$ and $R_4$, which can be the same or different, are, independently, H, OH, O, $OOCH_3$, $OOCH_2CH_3$, $OCH_3$, or $OC_2H_5$, and $R_3$ and $R_4$ together are an ether or a lactone, which may optionally contain a double bond $\Delta^{7(8)}$ or $\Delta^{8(8')}$. The compound of Formula I can also be used for the preparation of a medicament or for the preparation of a medicament for the treatment of a condition as described herein.

The carbons at positions 9 and 9' of the compounds of Formula I have a cis configuration, i.e. the 8-9 and 8'-9' bonds are located in or above the plane of the carbon ring (beta bonds), as indicated by the solid lines in the Formula I. A wavy line, as between the carbons 1' and 7', indicates that the bond can be either an alpha or a beta bond. An alpha bond, that is below the plane of the carbon ring, is illustrated by a dashed line. The benzene ring should preferably be in α-position, as is demonstrated by picropodophyllin, deoxypicropodophyllin, α-apopicropodophyllin, and β-apopicropodophyllin.

Picropodophyllin Derivatives Useful in the Methods of the Invention

Picropodophyllin derivatives suitable for use in the invention include but are not limited to hydrates, polymorphs, glycosides, prodrugs, isomers, epimers, salts, esters and analogs, that have for example, ring modifications or ring substitutions. Non-limiting examples of substitutions include methylation, hydroxylation, hydroxymethylation, trifluoromethoxylation, methoxylation and halogenation. The derivatives include but are not limited to 3'-demethoxy-picropodophyllin, 4'-demethoxy-picropodophyllin, 5'-demethoxy-picropodophyllin, 3',4'-didemethoxy-picropodophyllin, 3',5'-didemethoxy-picropodophyllin, 4,5'-didemethoxy-picropodophyllin, 3',4',5'-tridemethoxy-picropodophyllin, deoxypicropodophyllin, epipicropodophyllin, 4β-azidopicropodophyllin, α-apopicropodophyllin, β-apopicropodophyllin, α-peltatin, β-peltatin, demethoxyepiisopicropodophyllin, etoposide, teniposide, tafluposide, etopophos, NK611, GL-331, NPF, TOP-53 and their derivatives. Some of these derivatives are described by Vitale et al. (*Journal of Organic Chemistry* 73:5795-5805, 2008; Nagar et al., *Pharmacophore* 2(2):124-134, 2011; U.S. Pat. Nos. 5,739,114; 7,629,381; 7,709,526; 8,158,809; 8,389,747; United States Patent Application Publication Nos. 0520050009759, US20090271879; US20100216728; and International Patent Application Publication Nos. WO 2013132262, WO 2013132263. The content of the U.S. patents and published patent applications are incorporated herein by reference.

Vitale et al. (*Journal of Organic Chemistry*, 73:5795-5805, 2008) describe vinyl-lactones and aryltetralin lignan derivatives that are useful in the present methods. Axelson and Bremberg (WO 2013/132262 and WO 2013/132263) have described analogs of picropodophylin useful in the methods of the current invention. These analogs can be defined by the following structure:

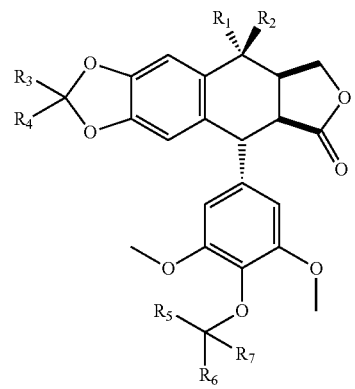

wherein
$R_1$ is OH, H, D or —O—C(O)—$C_1$-$C_6$ alkyl;
$R_2$ is H or D
$R_3$ and $R_4$ is each and independently H or D
$R_5$, $R_6$ and $R_7$ is each and independently H or D
Exemplary picropodophyllin analogs described by Axelson and Bremberg useful in the methods of the current invention include but are not limited to:
(5R,5aR,8aS,9R)-8-oxo-9-(3,4,5-trimethoxyphenyl)-5,5a,6,8,8a,9-hexahydrofuro[3,4':6,7]naphtho[2,3-d][1,3]dioxol-5-yl acetate;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl propanoate;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl pentanoate;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl heptanoate;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl undecanoate;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl palmitate;
3-oxo-3-(((5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl)oxy)propanoic acid;
9-oxo-9-(((5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl)oxy)nonanoic acid;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl 2-((((9H-fluoren-9-yl)methoxy)carbonyl)amino)acetate;
(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl 2-aminoacetate;

(R)-(5R,5aR,8aS,9R)-8-oxo-9-(3,4,5-trimethoxyphenyl)-5, 5a,6,8,8a,9-hexahydrofuro[3',4':6,7]naphtho[2,3-d][1,3] dioxol-5-yl 2-((((9H-fluoren-9-yl)methoxy)carbonyl) amino)-3-methyl butanoate;

(R)-(5R,5aR,8aS,9R)-8-oxo-9-(3,4,5-trimethoxyphenyl)-5, 5a,6,8,8a,9-hexahydrofuro[3',4':6,7]naphtho[2,3-d][1,3] dioxol-5-yl 2-amino-3-methylbutanoate;

(R)-(5R,5aR,8aS,9R)-8-oxo-9-(3,4,5-trimethoxyphenyl)-5, 5a,6,8,8a,9-hexahydrofuro[3',4':6,7]naphtho[2,3-d][1,3] dioxol-5-yl 2-((((9H-fluoren-9-yl)methoxy)carbonyl) amino)-4-methylpentanoate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl (2S)-2-amino-4-methylpentanoate;

(2R,3S)-(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl 2-((((9H-fluoren-9-yl)methoxy)carbonyl)amino)-3-methylpentanoate;

(2R,3S)-(5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl-2-amino-3-methyl pentanoate;

Methyl((5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl) carbonate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl dimethylcarbamate;

bis((5R,5aR,8aS,9R)-8-oxo-9-(3,4,5-trimethoxyphenyl)-5, 5a,6,8,8a,9-hexahydrofuro[3',4':6,7]naphtho[2,3-d][1,3] dioxol-5-yl) nonanedioate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 4-methylbenzoate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 3-(4-methoxyphenyl)propanoate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl isoxazole-5-carboxylate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 2-(2,5-difluorophenyl)acetate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 2-((tertbutoxycarbonyl)amino)propanoate;

Methyl((5R,5aR,8aS,9R)-8-oxo-9-(3,4,5-trimethoxyphenyl)-5,5a,6,8,8a,9-hexahydrofuro[3',4':6,7]naphtho[2,3-d][1,3]dioxol-5-yl) fumarate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 2-(3-bromophenyl)acetate;

(5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 2-(4-methylphenylsulfonamido)acetate; and (5R,5aR,8aS,9R)-8-oxo-9-(3,4,5-trimethoxyphenyl)-5,5a,6, 8,8a,9-hexahydrofuro[3',4':6,7]naphtho[2,3-d][1,3]dioxol-5-yl 2,2-dimethyl-5-oxotetrahydrofuran-3-carboxylate.

Berkowitz et al. (U.S. Patent Application Publication No. 20090271879) describe yet other analogs useful in the methods of the current invention. These analogs are defined by the formula:

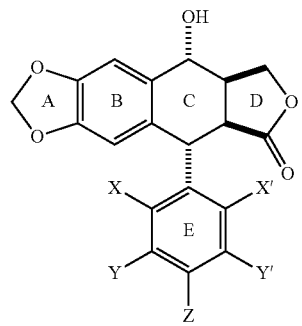

wherein X, X', Y, Y' and Z may be independently hydrogen; deuterium; tritium; a $C_1$-$C_8$ saturated or unsaturated, alkyl or cycloalkyl group; a hydroxyl group; an ether-protected hydroxyl group bearing a $C_1$-$C_8$ saturated or unsaturated alkyl or cyclic alkyl group; a carboxylate ester-protected hydroxyl group derived from a $C_1$-$C_8$ saturated or unsaturated, cyclic or acyclic, carboxylic acid; a hydroxyl group protected as a phosphate mono-, di- or triester, the di-, or triester having $C_1$-$C_4$ saturated or unsaturated alkyl group(s); a $C_1$-$C_8$ alkoxy, a $C_1$-$C_4$ alkoxy; a phosphonate mono- or diester-protected hydroxyl group derived from a $C_1$-$C_8$ saturated or unsaturated, cyclic or acyclic, phosphonic acid wherein the diester also contains a $C_1$-$C_8$ saturated or unsaturated alkyl group; a phosphinate ester-protected hydroxyl group derived from a phosphinic acid bearing two $C_1$-$C_8$ saturated or unsaturated, cyclic or acyclic, alkyl groups; a hydroxyl group protected as a sulfate mono- or diester bearing a $C_1$-$C_4$ saturated or unsaturated alkyl group; a hydroxyl group protected as a sulfonate ester derived from a sulfonic acid bearing a $C_1$-$C_8$ saturated or unsaturated, cyclic or acyclic, alkyl group; an amino group; a primary or secondary amine bearing 1 to 2 $C_1$-$C_8$ saturated or unsaturated alkyl group(s), respectively; a carboxamide-protected, unsubstituted or primary amine bearing a $C_1$-$C_4$ saturated or unsaturated alkyl group; an amino group derived from a $C_1$-$C_8$ saturated or unsaturated, cyclic or acyclic, carboxylic acid; a carboxylic acid; a carboxylate ester bearing a $C_1$-$C_4$ saturated or unsaturated alkyl group; a phosphonic acid; a phosphonatemono- or diester bearing 1 to 2 $C_1$-$C_4$ saturated or unsaturated alkyl group(s), respectively; a phosphinic acid having a $C_1$-$C_8$ saturated or unsaturated, cyclic or acyclic, alkyl group or ester bearing a $C_1$-$C_4$ saturated or unsaturated alkyl group; a formyl group; an acetyl group; a benzoyl group; a carboxamide group derived from ammonia or from a primary or secondary amine bearing 1 to 2 $C_1$-$C_4$ saturated or unsaturated alkyl group(s), respectively; a sulfhydryl group; a thioether bearing a $C_1$-$C_8$ saturated or unsaturated, cyclic or acyclic, alkyl group; a sulfonic acid, a sulfonate ester bearing a $C_1$-$C_4$ saturated or unsaturated alkyl group; an alkylsulfonyl group bearing a $C_1$-$C_8$ saturated or unsaturated, cyclic or acyclic, alkyl group; a phenylsulfonyl group; a sulfoxide bearing a $C_1$-$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group with the proviso that when X and X' are H, Y, Y', and Z cannot all be methoxy. The preferred derivatives, described in US 20090271879, that are useful in the methods of the current invention are:

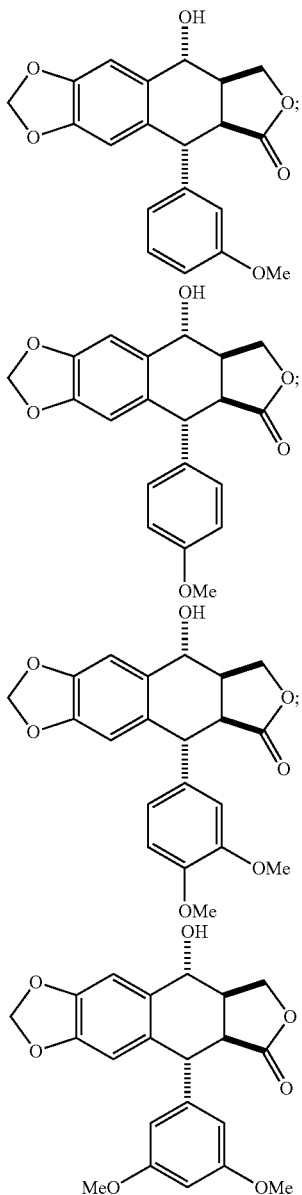

Synthesis of Picropodophyllin and Derivatives Useful in the Methods of the Invention Picropodophyllin may also be precipitated by decomposing podophyllin in an alkali or generated by microbes using methods known to one of ordinary skill in the art (for example, see Stadler and Bach, *Angew. Chem, Int. Ed. Engl.*, 47(39):7557, 2008). For example, *Penicillium* strains can isomerize podophyllotoxin to picropodophyllin (Guo et al., *J. Asian Nat. Prod. Res.* 1(2):99-102, 1998). Other methods for synthesis of picropodophyllin suitable for current invention include but are not limited to enzyme-assisted asymmetric total synthesis of (−)-picropodophyllin, reviewed by Berkowitz et al. (*J. Org. Chem.* 65:847-860, 2000); United States Patent Application Nos. US20090271879 and US 20130245285; Vitale et al., (*Journal of Organic Chemistry*, 73:5795-5805, 2008).

Berkowitz et al., (*J. Org. Chem.* 65:847-860, 2000) describe enzyme-assisted asymmetric total synthesis of (−)-picropodophyllin that features achievement of asymmetry using stereospecificity of enzymes to catalyze desymmetrization of advanced meso diacetate intermediate. The precursor used in this method is piperonal, which is converted via bromination, acetalization, and halogen-metal exchange/hydroxymethylation to an isobenzofuran intermediate (IBF). Treatment of this intermediate with HOAc with pure dimethyl maleate results in a 2.8:1 endo:exo mixture of maleate IBF Diels-Alder adducts. Alternatively, the desired endo meso diester is obtained using dimethyl acetylene dicarboxylate as the dienophile, followed by catalytic hydrogenation. Reduction of the desired endo meso diester using LiAlH$_4$ leads to formation of a meso diol intermediate, which is then converted to the corresponding meso diesters by treatment with Ac$_2$O, BzCl, and PhCH$_2$COCl. A suitable acyl transfer enzymes is then used in the next step to introduce asymmetry, yielding a key chiral intermediate. Use of s specific protecting groups and Swern oxidation leads to an aldehyde intermediate, which produces dihydronaphthalene intermediates having properly set C3 and C4 stereocenters using retro-Michael ring opening; which is then subjected to conjugate addition using a arylcopper reagent derived from (3,4,5-trimethoxy)phenylmagnesium bromide and CuCN. The conjugate is then subjected to lactonization and SEM deprotection to yield (−)-picropodophyllin.

Another method of synthesis of picropodophyllin useful in the methods of the current invention is described by Axelsson et al. (United States Patent Application No. US 20130245285). This method is based on the following epimerization reaction using Heck reaction conditions:

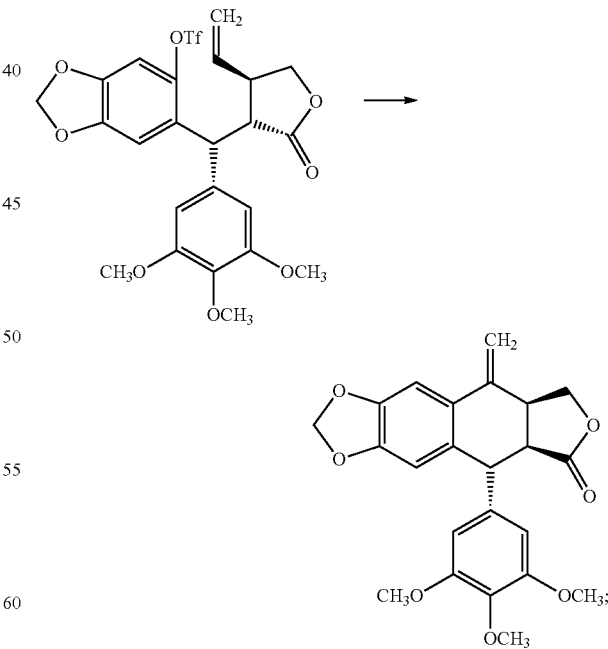

followed by cyclization in the presence of a base; a protic solvent or a mixture of a protic and an aprotic solvent; and a transition metal component one-pot reaction; wherein, P is an activating group;

R may be the same or different, is OH, OCH$_3$, OCH$_2$CH$_3$, F, Cl, CH$_3$ or CF$_3$; and n is 0, 1, 2, 3, or 4.

Vitale et al. (*Journal of Organic Chemistry*, 73:5795-5805, 2008) describe synthesis of certain picropodophyllin analogs useful in the methods of the current invention. These analogs are synthesized by Pd-catalyzed intramolecular allylic alkylation of unsaturated malonyl esters to give 4-vinyl-substituted γ-lactones, only with a substrate incorporating a suitably positioned silicon moiety. This intermediate is further subjected to ionization toward the desired η3-allylpalladium complex resulting 4-[dimethyl-(2-thienyl)silylvinyl] lactone; which is subsequently engaged into Hiyama couplings with various iodoarenes, to give the corresponding 4-(R-styryl)-γ-lactones. Specifically substituted iodoarene is used to generate advanced tetracyclic lactone intermediate derivatives of lignans belonging to the podophyllotoxin family, which are then converted to picropodophyllin analogs by electrophilic aromatic substitution with a variety of electron-rich arenes.

The invention especially refers to the use of compounds of Formula II or a pharmaceutically or physiologically acceptable derivative thereof:

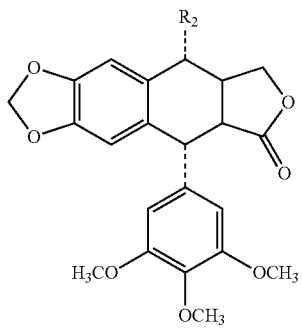

In Formula II, R$_2$ can be H, OH, O, OOCH$_3$, OOCH$_2$CH$_3$, OCH$_3$, or OC$_2$H$_5$. Formulas I and II encompass picropodophyllin, which is known to have active medicinal properties. It is naturally found in small amounts in the rhizome or stem of the perennial herb plant American Mayapple (*Podophyllum peltatum*), commonly referred to by many other names, such as Indian apple, and *Podophyllum emodi*, also called *Podophyllum hexandrum*, Himalyan mayapple or Indian mayapple. The compounds can be generated by synthetic methods known in the art.

Methods of the Invention

Podophyllin is a resin that may be extracted from the rhizome and roots of the same herb plants described above, and both podophyllin and picropodophyllin are cyclolignans (phytoestrogens characterized by a pair of propylbenzene groupings) having an additional ring structure. Podophyllin is well known for its ability to remove genital warts. It also has anti-cancer activities, but its use is somewhat limited because of its toxicity profile. A purified form, podofilox (tradenames: Condylox and Wartec solution) is currently available for the treatment of warts.

Picropodophyllin has more recently been shown, in WO 02/102804, to be an potent inhibitor of the insulin-like growth factor-1 (IGF-1). IGF-1 is a hormone that binds to the insulin-like growth factor 1 receptor (IGF1R) and the insulin receptor with a higher affinity for the former. IGF1R is a tyrosine kinase receptor and activates the AKT signaling pathway as well as other signaling pathways. Activation of IGF is important in mediating cell growth and proliferation. It is also an inhibitor of apoptosis. IGF-1, in large part, mediates the effects of growth hormone, promoting growth in almost every cell in the body.

As noted, the methods of the invention can include the administration of a pharmaceutically acceptable salt of a compound described herein. For example, the salt can be an acid-addition salt (e.g., a salt formed with an inorganic acid), an alkali metal salt (e.g., an alkaline earth metal salt), or a salt formed with an organic base. Useful salts include acetate, fumarate, maleate, tartrate, citrate, hydrochloride, hydrobromide, sulphate and phosphate salts. Hydrates of picropodophyllin include podophyllic acid.

In some aspects the current invention include method of treatment of skin diseases or skin conditions comprising administration of a composition comprising picropodophyllin, another compound described herein, and/or a pharmaceutically acceptable precursor or prodrug precursor or prodrug thereof, wherein the skin condition is verruca (warts), common warts (verruca vulgaris), flat warts (verruca plana), genital warts (condyloma accuminatum), certain types of ichthyosis, psoriasis, actinic keratosis, condyloma, molluscum contagiosum, acanthosis nigricans, porokeratosis, seborrheic keratosis, fibroepithelial polyp (skin tag), melasma, and malignant hyperproliferative skin conditions including angiosarcoma, Kaposi's sarcoma, sarcoma, or dermatofibrosarcoma protuberans, squamous cell carcinoma, basal cell carcinoma, squamous cell carcinoma in situ (Bowen's disease), and melanoma.

In certain embodiments, the methods of treating skin diseases or skin conditions comprise administering a composition comprising one or more picropodophyllin derivatives described by Vitale et al. (*Journal of Organic Chemistry*, 73:5795-5805, 2008), including the vinyl-lactones and aryltetralin lignan derivatives.

In certain embodiments, the method of treatment of skin diseases or skin conditions comprising administration of a composition comprising picropodophyllin derivatives described by Axelson and Bremberg (WO 2013/132262 and WO 2013/132263); wherein the skin diseases or skin conditions is verruca (warts), common warts (verruca vulgaris), flat warts (verruca plana), genital warts (condyloma accuminatum), certain types of ichthyosis, psoriasis, actinic keratosis, condyloma, molluscum contagiosum, acanthosis nigricans, porokeratosis, seborrheic keratosis, fibroepithelial polyp (skin tag) or melasma.

In certain embodiments of the invention, skin diseases or skin conditions of the current invention include skin diseases or skin conditions other than cancer.

In certain embodiments of the invention, skin diseases or skin conditions of the current invention include skin diseases or skin conditions other than malignant hyperproliferative skin conditions.

In certain embodiments of the invention, skin diseases or skin conditions of the current invention includes one or plurality skin diseases or skin conditions selected from the group consisting of verruca (warts), common warts (verruca vulgaris), flat warts (verruca plana), genital warts (condyloma accuminatum), certain types of ichthyosis, psoriasis, actinic keratosis, condyloma, molluscum contagiosum, acanthosis nigricans, porokeratosis, seborrheic keratosis, fibroepithelial polyp (skin tag), melasma, and malignant hyperproliferative skin conditions including angiosarcoma, Kaposi's sarcoma, sarcoma, or dermatofibrosarcoma protuberans, squamous cell carcinoma, basal cell carcinoma, squamous cell carcinoma in situ (Bowen's disease), and melanoma.

In some aspects, the current invention includes use of picropodophyllin, another compound described herein, and/or a pharmaceutically acceptable precursor or prodrug thereof in preparation of a medicament for treatment of skin diseases or skin conditions wherein the skin diseases or skin conditions is verruca (warts), common warts (verruca vulgaris), flat warts (verruca plana), genital warts (condyloma accuminatum), certain types of ichthyosis, psoriasis, actinic keratosis, condyloma, molluscum contagiosum, acanthosis nigricans, porokeratosis, seborrheic keratosis, fibroepithelial polyp (skin tag), melasma, and malignant hyperproliferative skin conditions including angiosarcoma, Kaposi's sarcoma, sarcoma, or dermatofibrosarcoma protuberans, squamous cell carcinoma, basal cell carcinoma, squamous cell carcinoma in situ (Bowen's disease), or melanoma.

In certain embodiments, the medicament comprises one or more picropodophyllin derivatives as described by Vitale et al., (*Journal of Organic Chemistry*, 73:5795-5805, 2008), including the vinyl-lactones and aryltetralin lignan derivatives.

In certain embodiments, the medicament comprises picropodophyllin derivatives described by Axelson and Bremberg (WO 2013/132262 and WO 2013/132263); wherein the skin diseases or skin conditions is verruca (warts), common warts (verruca vulgaris), flat warts (verruca plana), genital warts (condyloma accuminatum), certain types of ichthyosis, psoriasis, actinic keratosis, condyloma, molluscum contagiosum, acanthosis nigricans, porokeratosis, seborrheic keratosis, fibroepithelial polyp (skin tag) or melasma.

In certain embodiments, the current invention includes use of picropodophyllin, another compound described herein, and/or a pharmaceutically acceptable precursor or prodrug thereof in preparation of a medicament for treating skin diseases or skin conditions of the current invention include skin diseases or skin conditions other than cancer.

Pharmaceutical Formulations, Doses, and Administration: Pharmaceutical compositions for use in accordance with the present invention may be formulated in a conventional manner using one or more physiologically acceptable carriers or excipients. For example, a solution can be prepared as in the Example provided below with a 100% propylene glycol solution. After dissolution in an appropriate vehicle, additional preparations could include a gel, cream, ointment, foam, aerosol, adhesive patch, spray, or powder. Although picropodophyllin is nearly completely insoluble in water, solutions for pharmacologic use can be prepared by dissolving crystallized material in alcohol (such as ethanol or isopropanol), chloroform, DMSO, (glacial) acetic acid, hot fatty oils, and ether.

Any suitable concentration of an active pharmaceutical ingredient may be used, where the active pharmaceutical ingredient is administered in an effective amount to achieve its intended purpose. Determination of a therapeutically effective amount for a particular active ingredient is well within the capability of persons skilled in the art.

The specific therapeutically effective dose level for any particular patient will depend upon a variety of factors including activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent. In general, the dose may comprise 0.01 mg to about 1 g/kg/day.

In general, the dose may depend on factors such as exact compound used in the methods of the current invention, type of formulation used, indication being treated, severity of symptoms, mode of administration, age and sex of the subject etc. In some embodiments, a topical formulation of the pharmacologic agent can be applied to any skin area in need of treatment, for example, a skin area of between 1 and 400 cm$^2$, or any other area within the recited range, for example, 25, 50, 75, 100, 125, 150, 175, 200, 225, 250, 275, 300, 325, 350, 375, or 400 cm$^2$.

The pharmacologic compositions comprising picropodophyllin or derivatives thereof may contain from about 0.001% to about 10% picropodophyllin or a derivative (weight/volume), for example, from about 0.1 to 2.5%, 0.1 to 5%, 2.5 to 5.0%, 0.5 to 2.5%, or from about 0.5 to 5% (weight/volume). In some embodiments, the concentration picropodophyllin or a derivative thereof may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5 or about 10.0% picropodophyllin or a derivative thereof (weight/volume), or any other dose within any recited range, or any range between any two recited values.

For parenteral administration (e.g., subcutaneous, intramuscular, intravenous), the dose of picropodophyllin or a derivative thereof may be about 0.05 mg/kg/day to about 20 mg/kg/day. For example, the dose may be may be about 0.05 mg, about 0.06 mg, about 0.07 mg, about 0.08 mg, about 0.09 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.6 mg, about 1.7 mg, about 1.8 mg, about 1.9 mg, about 2 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about, 3.1 mg, about 3.2 mg, about 3.3 mg, about 3.4 mg, about 3.5 mg, about 3.6 mg, about 3.7 mg, about 3.8 mg, about 3.9 mg, about 4 mg, about, 4.1 mg, about 4.2 mg, about 4.3 mg, about 4.4 mg, about 4.5 mg, about 4.6 mg, about 4.7 mg, about 4.8 mg, about 4.9 mg, about 5 mg, about, 5.1 mg, about 5.2 mg, about 5.3 mg, about 5.4 mg, about 5.5 mg, about 5.6 mg, about 5.7 mg, about 5.8 mg, about 5.9 mg, about 6 mg, about, 6.1 mg, about 6.2 mg, about 6.3 mg, about 6.4 mg, about 6.5 mg, about 6.6 mg, about 6.7 mg, about 6.8 mg, about 6.9 mg, about 7 mg, about 7.5 mg, about 8 mg, about 8.5 mg, about 8 mg, about 8.5 mg, about 10 mg, about 10.5 mg, about 11 mg, about 12 mg, about 13 mg, about 14 mg, about 15 mg, about 16 mg, about 17 mg, about 18 mg, about 19 mg, about 20 mg or any other dose within the recited range, or any range between any two recited doses. A patient may receive this dose as a single bolus or infusion over 1, 2, 3, 4-6, 6-10 hours, once, twice, thrice, or 4-6 times a day. The treatment may be continued from anywhere between one day and two years.

For oral administration, the dose may be about 0.5 mg/day to about 10000 mg/day. For example, the dose may be may be about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 30 mg, about 35 mg, about 40 mg, about 45 mg, 50 mg, about 55 mg, about 60 mg, about 65 mg, about 70 mg, about 75 mg, about 80 mg, about 90 mg, about 100 mg, about 105 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 550 mg, about 600 mg, about 650 mg, about 700 mg, about 750 mg, about 800 mg, about 850 mg, about 900 mg, about 950 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 3300 mg, about 3400 mg, about 3500 mg, about 3600 mg, about 3700 mg, about 3800 mg, about 3900 mg, about 4000 mg, about 4100 mg, about 4200 mg, about 4300 mg, about 4400 mg, about 4500 mg, about 4600 mg, about 4700 mg, about 4800 mg, about 4900 mg, about 5000 mg, about 5100 mg, about 5200 mg, about 5300 mg, about 5400 mg, about 5500 mg, about 5600 mg, about 5700 mg, about 5800 mg, about 5900 mg, about 6000 mg, about 6100 mg, about 6200 mg, about 6300 mg, about 6400 mg, about 6500 mg, about 6600 mg, about 6700 mg, about 6800 mg, about 6900 mg, about 7000 mg, about 7100 mg, about 7200 mg, about 7300 mg, about 7400 mg, about 7500 mg, about 7600 mg, about 7700 mg, about 7800 mg, about 7900 mg, about 8000 mg, about 8100 mg, about 8200 mg, about 8300 mg, about 8400 mg, about 8500 mg, about 8600 mg, about 8700 mg, about 8800 mg, about 8900 mg, about 9000 mg, about 9100 mg, about 9200 mg, about 9300 mg, about 9400 mg, about 9500 mg, about 9600 mg, about 9700 mg, about 9800 mg, about 9900 mg, about 10000 mg, or any other dose within the recited range. A patient may receive this dose as a tablet, capsule, or other suitable oral administration form, once, twice, thrice, or 4-6 times a day. The treatment may be continued from anywhere between one day and two years.

The compounds described herein may be administered directly, they may also be formulated to include at least one pharmaceutical acceptable carriers, diluents, excipients, adjuvants, fillers, buffers, preservatives, lubricants, solubilizers, surfactants, wetting agents, masking agents, coloring agents, flavoring agents, and sweetening agents. Also, as described herein, such formulation may also include other active agents, for example, other therapeutic or prophylactic agents.

Methods of making a pharmaceutical composition include admixing at least one active compound, as defined above, together with one or more other pharmaceutically acceptable ingredients, such as carriers, diluents, excipients, and the like. When formulated as discrete units, such as tablets or capsules, each unit contains a predetermined amount of the active compound.

An acceptable carrier refers to those carriers that cause at most, little to no irritation, provide suitable preservation if needed, and deliver picropodophyllin and/or one or more of its metabolites, analogs or precursors of the present invention in a homogenous dosage. Pharmaceutically acceptable carriers can include any and all solvents, dispersion media, coatings, antibacterial and antifungal agents, isotonic and absorption delaying agents, and the like that are physiologically compatible, sterile aqueous solutions or dispersions and sterile powders for the extemporaneous preparation of sterile injectable solutions or dispersion. The use of such media and agents for pharmaceutically active substances is well known in the art. Supplementary active compounds can also be incorporated into the compositions.

For pulmonary delivery, picropodophyllin and/or one or more of its metabolites, analogs or precursors may be combined with pulmonary acceptable preservatives, co-solvents, surfactants, viscosity enhancers, penetration enhancers, buffers, sodium chloride, or water to form an aqueous, sterile suspension or solution.

The formulations may be prepared by any methods well known in the art of pharmacy. The formulation may be prepared to provide for rapid or slow release; immediate, delayed, timed, or sustained release; or a combination thereof. Formulations may be in the form of liquids, solutions, suspensions, emulsions, elixirs, syrups, electuaries, mouthwashes, drops, tablets, granules, powders, lozenges, pastilles, capsules, gels, pastes, ointments, creams, lotions, oils, foams, sprays, mists, or aerosols. Formulations may be provided as a patch, adhesive plaster, bandage, dressing, or in the form of depot or reservoir. Many methods for the preparation of such formulations are known to those skilled in the art.

Routes of Administration:

In certain embodiments, pharmaceutical compositions of the present invention may be formulated for administration by any route of administration, including but not limited to systemic, peripheral, or topical. Illustrative routes of administration include, but are not limited to, oral, such as by ingestion, buccal, sublingual, transdermal including, such as by a patch, plaster, and the like, transmucosal including, such as by a patch, plaster, and the like, intranasal, such as by nasal spray, ocular, such as by eye drops, pulmonary, such as by inhalation or insufflation therapy using, such as via an aerosol through the mouth or nose, rectal, such as by suppository or enema, vaginal, such as by pessary, parenteral, such as by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and by implant of a depot or reservoir, such as intramuscularly, topical including, such as by cream, gel, ointment, lotion, solution and the like. Methods of preparing pharmaceutical formulations are well known in the art. Dosage of the pharmaceutical compositions may vary by route of administration. Certain administration methods may include the step of administering the composition one or more times a day to obtain the desired therapeutic effect.

Picropodophyllin and/or its derivatives can be formulated for oral delivery as a solution, gelatin capsule, or tablet. The oral liquid formulations and capsule formulations are well known to one of ordinary skill in the art. The tablet formulation can include: 1-80% picropodophyllin or a derivative thereof; 10-90% fillers, disintegrants, lubricants, glidants, binders; and 1-20% additional compounds that ensure easy disintegration, disaggregation, and dissolution of the tablet in the stomach or the intestine.

The tablet may be formulated for immediate release, sustained release, or delayed or modified release. The tablet may be optionally coated can make the tablet resistant to the stomach acids and it disintegrates in the duodenum, jejunum and colon as a result of enzyme action or alkaline pH. These formulations are well known to one of ordinary skill in the art. The tablets may be further coated with sugar, varnish, or wax to mask the taste.

An exemplary tablet formulation contains: 5-50% picropodophyllin; acids, bases or salts thereof such as citric acid and sodium citrate; a solvent like glycerin or propylene glycol, alcohol, or water; one or more of polyethylene glycol, polyvinylpyrrolidone, dextran, polyacrylic acid, polyethylene oxide, starches, cellulose or modified cellulose (such as methylcellulose, carboxymethyl cellulose, hydroxymethyl cellulose, hydroxyethyl cellulose, hydroxypropyl methylcellulose, microcrystalline cellulose, hydroxypropyl cellulose), sucrose, lactose, xylitol, sorbitol or maltitol; and pharmaceutically acceptable gelatin or modified gelatin.

Alternatively, picropodophyllin or its derivatives may be formulated for parenteral delivery by a route such as intravenous, subcutaneous, intramuscular, and intra-articular administration. These formulations are either liquids or lyophilizates. The liquid or lyophilized formulations comprise of 1-50% picropodophyllin or its derivatives and remaining ingredients selected from solubilizers, stabilizers, buffers, tonicity modifiers, bulking agents, viscosity enhancers/reducers, surfactants, chelating agents, and adjuvants. These ingredients are well known to one of ordinary skill in the art. Lyophilized formulations need to be reconstituted prior to administration. Liquid formulations are optionally diluted with pharmaceutically acceptable diluents such as 5% Dextrose Injection, USP or 0.9% Sodium Chloride Injection, USP. These formulations are preferably administered by infusion although bolus administration is also possible.

An exemplary formulation comprises: picropodophyllin or its derivatives; one or more of sodium citrate, polyvinylpyrrolidone and hydroxypropylcellulose and polyethylene glycol, methylcellulose, propylene glycol, peanut oil, benzyl alcohol, N,N-dimethylacetamide, polyoxyethylated castor oil, dehydrated alcohol, and water.

Alternatively, picropodophyllin or its derivatives may be formulated for topical delivery in the form of a collodion, cream, emulsion, foam, gel, lotion, ointment, paste, solution, or powder. These formulations are well known to one of ordinary skill in the art.

An exemplary formulation comprises: picropodophyllin or a derivative thereof; one or more of benzoine tincture, benzoine Sumatra tincture, hard paraffin, soft paraffin, microcrystalline wax, ceresine, wool fat, beeswax, emulsifying wax, cetrimide, N,N-dimethylacetamide, benzyl alcohol, polyvinylpyrrolidone, hydroxypropylcellulose, polyethylene glycol, methylcellulose, propylene glycol, olive oil, coconut oil, sesame oil, almond oil peanut oil, polyoxyethylated castor oil, dehydrated alcohol, and hydrocarbon bases including but not limited to white petrolatum, water.

In certain embodiments, picropodophyllin or a derivative thereof may be administered in form of a hydrogel. Gels are solid or semi-solid in appearance and still contain a high concentration of water. The gels may contain picropodophyllin or a derivative thereof or entrap granules containing them. The gels may optionally comprise of one or more of additional solvents, solutes, solubilizers, stabilizers, buffers, bulking agents, surfactants. The gels may contain additional drugs that reduce or prevent itching, swelling, pain, redness, and inflammation. They can optionally be configured for a slow or delayed release. The compounds described herein can be formulated in a hydrogel, and that hydrogel that may further include an additional protective film that is fully or partially air- and water-proof or air- and water-repellent and an adhesive surface that can be positioned, for example, around the periphery of the skin lesion that being treated. The methods of making hydrogels are well known in the art.

In some embodiments, compositions comprising picropodophyllin or a derivative thereof can be co-administered with other compounds or medications to either enhance its therapeutic effect or to minimize possible adverse effects. To increase its therapeutic effect it can be combined with a cytoxic agent, for example, fluorouracil or ingenol mebutate; a desquamating agent such as retinoic acid, an alpha hydroxyl acid (i.e., glycolic acid), or a beta hydroxyl acid (i.e., salicylic acid); or an immune stimulating compound such as imiquimod. To minimize adverse reactions such as inflammation, burning, and erythema picropodophyllin or a derivative thereof can be co-administered with a steroidal anti-inflammatory compound such as triamcinolone or hydrocortisone; a non-steroidal anti-inflammatory drug (NSAID) such as diclofenac sodium; a topical immunomodulator such as pimecrolimus; or an anti-pruritic agent such as pramoxine or menthol.

In certain further embodiments, modes of administration can include tablets, pills, capsules, injectables, topical application and aerosol all of which are capable of formulation by one of ordinary skill in the art.

In another embodiment, a method is provided for administering a therapeutically effective amount of picropodophyllin or one of its metabolites, analogs or precursors to treat one or more of the following skin or medical conditions: verruca (warts), actinic keratosis, condyloma, molluscum contagiosum, squamous cell carcinoma, basal cell carcinoma, squamous cell carcinoma in situ, melanoma, acanthosis nigricans, porokeratosis, seborrheic keratosis, fibroepithelial polyp (skin tag), melasma, angiosarcoma, Kaposi's sarcoma, sarcoma, acne (e.g., vulgaris, comedonal acne vulgaris, or cystic acne vulgaris) and conditions related thereto (e.g., scarring), perioral dermatitis, trichoepitheliomas and related genetic syndromes that cause multiple trichoepitheliomas. and dermatofibrosarcoma protuberans in a patient.

EXAMPLES

To date, 56 patients have been studied to determine the efficacy of picropodophyllin in treating actinic keratoses. The patients were randomized into four groups, and the patients in each group were treated with a solution containing either 0.5%, 1.25%, or 2.0% picropodophyllin (w/v) in propylene glycol, or a placebo constituting only the vehicle propylene glycol. The picropodophyllin solution was prepared in 100% propylene glycol solution. The solutions were prepared aseptically following GMP protocols. The affected areas of the body variously included the scalp, face, arms, and legs. Without knowing which one of the four solutions they were applying, the subjects self-applied one of the solutions to the skin. After initial application, the subjects gently massaged the solutions into their skin. This was done twice daily for 1 week. Lesions (actinic keratosis) were palpated and visualized by a trained lesion counter who is a board certified dermatologist. The same investigator evaluated each subject at each visit for consistency. The subjects were evaluated at baseline, day 3, day 7, day 14, day 28, day 56 and day 90. The results are shown in the Table below. Within the treatment area, the number of lesions were counted, regardless of their size. The change in the number of lesions (% decline from baseline) within the treatment area was calculated and the results are shown in the table below:

TABLE I

| [PPP] w/v | # Patients | # of Patients Completed to Date | | | % Decline from Baseline | | |
|---|---|---|---|---|---|---|---|
| | | 28 days | 56 days | 90 days | 28 days | 56 days | 90 days |
| 0.50% | 4 | 4 | 3 | 3 | $-56^{AB}$ | $-82^{AB}$ | $-90^{AB}$ |
| 1.25% | 23 | 13 | 10 | 5 | $-53^{AB}$ | $-73^{AB}$ | $-65^{AB}$ |
| 2.00% | 9 | 8 | 7 | 5 | $-17$ | $-55^{AB}$ | $-84^{AB}$ |
| Placebo | 20 | 18 | 16 | 14 | $-12$ | $-13$ | $-19^{B}$ |

[A] Indicates value is significantly different (p-value < 0.05) from Placebo
[B] Indicates value is significantly different (p-value < 0.05) from Baseline These results showed that compared to placebo, all the doses showed significant reduction in the number of lesions in the treatment area, as noted in Table I.

What is claimed is:

1. A method of treating actinic keratosis in a patient having actinic keratosis lesions, the method comprising administering, to the patient, a composition comprising a therapeutically effective amount of picropodophyllin, and/or a salt or hydrate thereof.

2. The method of claim 1, wherein the composition is formulated for topical administration to the patient's skin.

3. The method of claim 1, wherein the composition is formulated for administration by one or more of the following routes: oral, subcutaneous, intravenous, intramuscular, and nasal inhalation.

4. The method of claim 1, wherein the composition comprising a therapeutically effective amount of picropodophyllin and/or a salt, hydrate, active metabolite, analog, prodrug or other derivative thereof contains from about 0.1 to 5% (weight/volume) of picropodophyllin.

5. The method of claim 4, wherein the composition contains from about 0.5 to 2.5% (weight/volume) of picropodophyllin.

6. The method of claim 5, wherein the composition contains from about 0.5 to 2.0% (weight/volume) of picropodophyllin.

* * * * *